(12) United States Patent
Rogers et al.

(10) Patent No.: US 7,026,146 B2
(45) Date of Patent: Apr. 11, 2006

(54) ENCAPSULATION METHOD FOR MAINTAINING BIODECONTAMINATION ACTIVITY

(75) Inventors: Robert D. Rogers, Idaho Falls, ID (US); Melinda A. Hamilton, Idaho Falls, ID (US); Lee O. Nelson, Idaho Falls, ID (US); Jennifer Benson, Cockermouth (GB); Martin J. Green, Wooton (GB); Timothy N. Milner, Centerville, VA (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 625 days.

(21) Appl. No.: 10/217,925

(22) Filed: Aug. 12, 2002

(65) Prior Publication Data

US 2002/0192803 A1    Dec. 19, 2002

Related U.S. Application Data

(62) Division of application No. 09/606,563, filed on Jun. 29, 2000, now Pat. No. 6,465,706.

(60) Provisional application No. 60/142,351, filed on Jun. 30, 1999.

(51) Int. Cl.
  *C12N 11/04* (2006.01)
  *B09B 3/00* (2006.01)

(52) U.S. Cl. .................................. 435/182; 435/262.5

(58) Field of Classification Search .................. None
  See application file for complete search history.

(56) References Cited

U.S. PATENT DOCUMENTS

| 3,837,864 A | 9/1974 | Moraru et al. ............... 106/15 |
| 4,655,794 A | 4/1987 | Richardson et al. .......... 51/293 |
| 4,861,519 A | 8/1989 | Tusa et al. .................. 252/633 |
| 4,871,673 A | 10/1989 | Rehm et al. ................. 435/262 |
| 5,011,708 A | 4/1991 | Kelly et al. ................ 427/443.1 |
| 5,047,152 A | 9/1991 | Francis et al. ............... 210/611 |
| 5,152,341 A | 10/1992 | Kasevich .................... 166/248 |
| 5,264,018 A | 11/1993 | Koenigsberg et al. ........ 71/63 |
| 5,414,196 A | 5/1995 | Jennings ....................... 588/1 |
| 5,763,815 A | 6/1998 | Thomas et al. ............. 102/293 |
| 5,803,664 A | 9/1998 | Kawabata et al. .......... 405/128 |
| 5,839,079 A | 11/1998 | Benson et al. ................ 588/18 |
| 5,895,832 A | 4/1999 | Eccles ........................ 588/231 |
| 6,204,049 B1 * | 3/2001 | Bennett et al. .......... 435/254.1 |

FOREIGN PATENT DOCUMENTS

| DE | 3818777 C1 | 7/1989 |
| FR | 2 640 528 A1 | 6/1990 |
| FR | 2 674 890 A1 | 10/1992 |
| GB | 2 006 256 A | 10/1977 |
| JP | 02169093 A | 12/1998 |
| WO | WO 96/03754 A | 2/1996 |

OTHER PUBLICATIONS

Rogers, R. D., et al, "Industrialization of Phosphate Bioprocessing," *Beneficiation of Phosphates II*, 1999, Society for Mining, Metallurgy and Exploration, Inc., pp. 339-344.
Supplementary European Search Report dated Mar. 4, 2004, EP00946839.

* cited by examiner

*Primary Examiner*—David M. Naff
(74) *Attorney, Agent, or Firm*—Trask Britt, PC

(57) ABSTRACT

A method for maintaining the viability and subsequent activity of microorganisms utilized in a variety of environments to promote biodecontamination of surfaces. One application involves the decontamination of concrete surfaces. Encapsulation of microbial influenced degradation (MID) microorganisms has shown that MID activity is effectively maintained under passive conditions, that is, without manual addition of moisture or nutrients, for an extended period of time.

13 Claims, No Drawings

ENCAPSULATION METHOD FOR MAINTAINING BIODECONTAMINATION ACTIVITY

RELATED APPLICATION

This application is a divisional of application Ser. No. 09/606,563, filed Jun. 29, 2000, now U.S. Pat. No. 6,465,706, which claims the benefit of Provisional application Ser. No. 60/142,351, filed Jun. 30, 1999.

CONTRACTUAL ORIGIN OF THE INVENTION

The United States Government has certain rights in this invention pursuant to Contract No. DE-AC07-94ID13223, DE-AC07-13727, and Contract No. DE-AC07-05ID14517 between the United States Department of Energy and Battelle Energy Alliance, LLC.

BACKGROUND OF THE INVENTION

1. Field of the Invention

The present invention is directed generally to decontamination of cementitious surfaces. More specifically the present invention is related to a microbiological process for removing radioactive contamination from a concrete surface.

2. Relevant Technology

In the nuclear industry, concrete is commonly used to retain radioactive substances. There are thousands of nuclear facilities comprising about 50 square miles of radionuclide-contaminated concrete surfaces. These nuclear facilities use concrete ponds, canals, sumps, and other structures for the containment, transport, and storage of liquid and solid radioactive materials, resulting in the contamination of the concrete surfaces with radionuclides. Typically, the contamination is securely fixed on, or within one or two millimeters of the surface. Before the concrete is disposed of in a suitable waste disposal site, it is desirable to decontaminate the radio-active concrete surface.

One conventional method for decontamination entails dismantling the entire structure. However, all of the rubble from a dismantled structure must be disposed of as radiological waste even though the contaminated portions may comprise only the outer few millimeters. Another option involves manually chipping off only the outer few millimeters of the contaminated concrete. By either method, the cost to decommission and decontaminate the contaminated sites is estimated to be tens of billions of dollars.

In response to the significant need for an alternative cost-effective method for decontaminating a cementitious surface, U.S. Pat. No. 5,414,196 by Jennings, the entire disclosure of which is hereby incorporated herein by reference, is directed to microbial degradation of contaminated cement surfaces. The method comprises applying a microorganism, such as a species of thiobaccillus, to degrade the surface of the concrete and thereby release a material comprising the radioactive substance. The released material is then removed from the surface by vacuum suction, scraping, brushing, or abrasion blasting. Once the concrete surface has been sufficiently decontaminated, the process may be stopped by heating or by depriving the microorganism of essential nutrients or moisture.

However, these same parameters (temperature, nutrients, and moisture) must be maintained at a level conducive to the growth of the bacteria in order for this method to perform effectively. For example, it is preferable that the cementitious surface contain a nutrient source such as sulphur. If the concrete does not contain sufficient nutrient, an alternate source of nutrient needs to be applied. Further, the needed moisture level must be maintained by periodic, manual addition of water.

Though such addition of moisture and nutrients is successful at maintaining active microbial influenced degradation of the concrete surfaces, manual addition is impracticable as the final method for maintaining the process under commercial application. Not only does this increase the cost and burden associated with decontaminating the various structures, it also increases the potential health and safety risks of the personnel responsible for the manual addition of moisture and nutrients.

SUMMARY AND OBJECTS OF THE INVENTION

It is therefore an object of the present invention to provide a method for maintaining microbial influenced degradation without the need for manual application of nutrients or moisture.

It is another object of the invention to provide a practical, cost effective, and environmentally acceptable method for decontaminating concrete.

A further object of the invention is to provide a method for decontaminating large surface concrete structures, hot cells, ponds, canals, sumps, biological shields, and other structures requiring decontamination through a naturally occurring microbial process.

These and other objects and features of the present invention will become more fully apparent from the following description and appended claims, or may be learned by the practice of the invention as set forth hereinafter.

To achieve the forgoing objects, and in accordance with the invention as embodied and broadly described herein, the present invention relates to a new and useful method for microbial influenced degradation of contaminated structures. The preferred method of the present invention is a biomediated process for removing contamination from a cementitious surface utilizing encapsulated microorganisms for the microbial influenced degradation. The encapsulated microorganisms of the present invention do not require the manual addition of moisture or nutrients to maintain conditions conducive to growth. Thus, the encapsulated microorganisms are simply sprayed or painted on to the contaminated surface and left for a period of time sufficient for microbial influenced degradation activity to degrade the cementitious surface to a selected depth.

The process preferably comprises applying a substantially uniform coating of the encapsulated microorganism to a contaminated cementitious surface. The microbial influenced degradation activity is preferably permitted to continue until the cementitious surface has been degraded to a desired depth. It has been demonstrated that radioactive contamination is usually localized in the first 1–2 mm of cementitious material. The degraded layer is preferably removed by brushing, washing or scrubbing the degraded cementitious surface.

DETAILED DESCRIPTION OF THE PREFERRED EMBODIMENTS

Biodecontamination of concrete surfaces is aimed at decontaminating concrete contaminated by radioactive and other hazardous compounds. Microbial influenced degradation (MID) has been demonstrated as an effective means for decontaminating concrete surfaces. When implemented, this technology has the potential of greatly reducing the costs compared to existing technologies which rely on physical/chemical removal, and disposal of contaminated portions of buildings and structures.

Biodecontamination has been shown to be effective under controlled conditions in laboratory and field applications. With the use of sulfur oxidizing bacteria, for example, decontamination occurs through the biogenic production of sulfuric acid which subsequently removes the contaminated concrete surface. Studies have shown that the key conditions for promoting active MID are maintaining an available source of reduced sulfur and providing a moist near-surface environment. However, the needed moisture level and sulfur concentration must be maintained by periodic, manual addition of water and elemental sulfur. Though this method is successful in maintaining active MID of the concrete surfaces, manual addition of moisture and nutrients is impracticable for commercial application.

Therefore, the present invention is directed to a method for the maintenance of appropriate levels of moisture and nutrients at the concrete surface without the need for additional manual applications thereof. Specifically, the method of the present invention utilizes encapsulation of MID microorganisms to eliminate the need for manual application of moisture and nutrients for degradation of contaminated cementitious surfaces.

The necessary components of the present invention include a microorganism, an encapsulation material, and a substrate such as a contaminated cementitious surface. Each of these components will be described individually herein prior to discussion of the method of the present invention. The terms "a," "an," and "the" as used in the specification and the appended claims include plural referents unless the context clearly dictates otherwise. Thus, a reference to "a microorganism" includes a reference to two or more of such microorganisms, "a bacteria" includes two or more of such bacteria, etc.

The microorganisms utilized in accordance with the present invention preferably belong to group capable of performing microbial influenced degradation. MID microorganisms typically grow under environmental conditions with temperatures ranging from 0° C. to 30° C. All MID microorganisms require the presence of moisture and appear to produce or be associated with biofilms that form on concrete surfaces.

Appropriate nutrient requirements vary according to the type of MID microorganism. The autotrophic mineral-acid-producing sulfur oxidizing bacteria and nitrifying bacteria require suitable forms of reduced sulfur or nitrogen, respectively, as sources of energy. The heterotrophic organic-acid-producing organisms require a suitable organic substrate such as glucose, starch, glycogen, cellulose, or the like.

Preferably, the MID microorganism utilized in accordance with the method of the present invention is an acid-producing bacterium or fungus, such as belongs to the group consisting of acid-producing heterotrophic bacteria and fungi, nitrifying bacteria, sulfur oxidizing bacteria, and mixtures thereof.

Nitrifying bacteria that can be used advantageously within the scope of the present invention include, but are not limited to, *Nitrosomonas* and *Nitrobacter* spp., such as *Nitrosomonas europea, Nitrobacter winogradskyi*, and *Nitrobacter vulgaris*. These nitrifying bacteria produce nitric acid that degrades cementitious surfaces.

Sulfur oxidizing bacteria that can be used advantageously within the scope of the present invention include, but are not limited to, *Thiobacillus* species such as *Thiobacillus thiooxidans, Thiobacillus ferrooxidans, Thiobacillus neapolitanus*, and *Thiobacillus intermedius*. These sulfur oxidizing bacteria produce sulfuric acid that degrades cementitious surfaces.

Organic-acid-producing heterotrophic bacteria and fungi that can be used advantageously within the scope of the present invention include, but are not limited to, numerous bacteria and fungi that produce acetic, citric, formic, lactic, and other carboxylic acids. Illustrative examples of such bacteria and fungi include bacteria from the genus Pseudomonas, such as *P. cepacia*, and fungi from the genera Aspergillus, such as *A. niger* and *A. phenicis, Penicillium*, such as *P. herquei, P. funiculosum, P. lanosocerulum, P. similicissum, P. atramentosum*, and *P. roquefortii, Paecilomyces, Acremonium, Verticillium, Geomyces*, and *Chrysosporium*.

It should be appreciated that other microorganisms capable of microbial influenced degradation are within the scope of the present invention.

The encapsulation material utilized in accordance with the present invention is combined with at least one type of MID microorganism, and includes a supply of appropriate nutrients and moisture. The resulting encapsulated microorganism requires no additional manual application of nutrients or moisture upon application to a contaminated surface for microbial influenced degradation. Thus, the encapsulated microorganism is referred to herein as being passively supplied with moisture and appropriate nutrients.

Suitable encapsulation materials for this invention are natural or synthetic polymeric binder materials. These materials should be able to encapsulate the microorganism, the moisture, and/or nutrients of this present invention in such a way that the nutrients and moisture are available to the microorganism and allow the microorganism to degrade the substrate on which they are applied. Examples of polymeric binder materials are natural and synthetic gels and foams. Natural and/or synthetic gelatin polymers are most preferred.

Preferred encapsulation materials are those which maintain sufficient adhesion to the substrate to adhere to the substrate during the degradation phase such as on a vertical surface, but which are readily removed at the end of the phase. The encapsulation materials preferably can be applied through spraying equipment, are non-toxic to the microorganisms, are gas permeable, hold their characteristics under acidic conditions, are easily applied and removed, and when dealing with radioactive contamination, are resistant to radioactivity.

Suitable examples of gels for encapsulation purposes include, but are not limited to, PrimaCel™, also known as EX-7948, Cellulon®, KelcoGel®, KELGIN®, KELZAN®, all by Monsanto Kelco Industrial Biopolymers. It should be appreciated that other gel-encapsulation materials which provide nutrients, moisture, or both, to the MID microorganisms, such as but not limited to foams or other viscous material, are within the scope of the present invention.

While conventional gels are formed at about 55° C. the preferred gel-encapsulation material, such as that used to encapsulate *T. thiooxidans* bacteria, is formed at a temperature of less than about 30° C. This relatively low temperature is used to avoid killing the bacteria.

A preferred gel-encapsulation material in accordance with the present invention comprises about 2 to about 5 grams of dry gel additive blended with about 500 to about 1000 ml of water, about 5 to about 30 grams of sulfur, and about 0.001 to about 0.1 grams of ammonium molybdo-phosphate. Alternatively, semi-dry gel additive is used in place of the dry additive. The mixture is blended in a high-shear mixer to produce a smooth, consistent gel, and then the microorganism, such as $T.$ $thiooxidans$, is added to the gel by way of a low-shear mixer. A preferred amount of microorganism is about $1\times10^9$ to about $1\times10^{11}$ per liter of the gel. The encapsulated microorganism is then ready to be utilized on a substrate.

A preferred substrate in accordance with the present invention is a contaminated cementitious surface. By definition, cementitious surfaces encompass surfaces having the characteristics of cement. A preferred cementitious surface suitable for the method of the present invention is concrete, examples of which occur in hot cells, ponds, canals, sumps, biological shields, and the like. It should be appreciated that the present invention is in no way limited to use with these specific cementitious surfaces or with cementitious surfaces in general.

Further, by way of example only and not limitation, the preferred cementitious surface for decontamination purposes is contaminated with toxic wastes, environmentally hazardous materials, radioactive materials, and/or other contaminants. Other contaminated surfaces degraded by microbial influenced degradation are also within the scope of the present invention.

To perform the method of the present invention, an effective amount of the encapsulated microorganism such as described above, is sprayed or painted in a substantially uniform coating on a contaminated surface. An effective amount means an amount of a encapsulated microorganism that is sufficient to provide a selected degradative effect and performance under selected parameters. A person of ordinary skill in the art should be able determine such an effective amount without undue experimentation according to the guidelines provided herein. One example of an effective amount of microorganism encapsulation-mixture is a sprayed thickness of about 1 mm to about 5 mm on a substrate.

In the case of a particularly "hot" radioactive area, the gel-encapsulated microorganism is preferably sprayed by means of remote application, which does not require the presence of an actual worker dressed in biological protective wear, and thus reduces exposure and risk.

The encapsulated microorganisms are preferably allowed to remain on the cementitious surface for an amount of time sufficient for microbial influenced degradation activity to degrade the cementitious surface to a selected depth. Those of skill in the art recognize that this sufficient amount of time will vary according to substrate and the depth required to eliminate the contaminated portions of the substrate. For example, microbial influenced degradation of a cementitious surface should extend up to about 4 mm, and preferably up to about 2 mm, into the surface to substantially degrade the contaminated layer. It has been demonstrated that a sufficient amount of time for this selected depth of degradation is about 12–18 months. It follows that an amount of time sufficient for microbial influenced degradation of less depth may take less time.

In a preferred embodiment of the present invention, the adaptability of a commercially available gel material, EX-7948, for the production of a hydrophilic gel matrix containing sulfur oxidizing MID microorganisms, sulfur, and water was demonstrated. The findings illustrate that this invention effectively maintains MID activity under passive conditions, that is, without manual addition of sulfur or water, for an extended period of time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An encapsulated microorganism comprising: a microorganism disposed in an encapsulating material including a gel additive, water, sulfur and ammonium molybdo-phosphate.

2. An encapsulated microorganism as recited in claim 1, wherein the microorganism comprises an acid-producing bacterium or fungus.

3. An encapsulated microorganism as recited in claim 1, wherein the microorganism is selected from the group consisting of acid-producing heterotrophic bacteria, heterotrophic fungi, nitrifying bacteria, sulfur oxidizing bacteria and mixtures thereof.

4. An encapsulated microorganism as recited in claim 3, wherein the gel additive, the water, the sulfur and the ammonium molybdo-phosphate are present in sufficient quantities to support microbial degradation for at least about 12 months.

5. An encapsulated microorganism as recited in claim 1, wherein the encapsulating material comprises:
   about 2 to about 5 grams of the gel additive;
   about 500 to about 1000 ml of the water;
   about 5 to about 30 grams of the sulfur;
   about 0.001 to about 0.1 grams of the ammonium molybdo-phosphate.

6. A process for encapsulating a microorganism comprising:
   providing an encapsulation material comprising a gel additive, water, sulfur and ammonium molybdo-phosphate; and
   adding a microorganism to the encapsulation material.

7. A process as in claim 6, wherein adding a microorganism to the encapsulation material further includes adding a microorganism that comprises an acid-producing bacterium or fungus.

8. A process as in claim 6, wherein adding a microorganism to the encapsulation material further includes adding a microorganism selected from the group consisting of acid-producing heterotrophic bacteria, heterotrophic fungi, nitrifying bacteria, sulfur oxidizing bacteria and mixtures thereof.

9. A process as recited in claim 6, wherein the encapsulation material comprises:
   about 2 to about 5 grams of the gel additive;
   about 500 to about 1000 ml of the water;
   about 5 to about 30 grams of the sulfur;
   about 0.001 to about 0.1 grams of the ammonium molybdo-phosphate.

10. A process as recited in claim 6, wherein the encapsulation material is formed at a temperature of less than about 30° C.

11. A process as recited in claim 6, wherein the microorganism is combined with the encapsulation material in a low shear mixing process.

12. A process as recited in claim 6, further comprising supplying nutrients to the microorganism-encapsulation material mixture.

13. A process as in claim 6, wherein providing an encapsulating material further comprises combining the gel additive, the water, the sulfur and the ammonium molybdo-phosphate in a high shear mixing process.

* * * * *